(12) United States Patent
Lampeter

(10) Patent No.: US 7,727,219 B2
(45) Date of Patent: Jun. 1, 2010

(54) STERILE SYSTEM AND METHODS FOR COLLECTING, TRANSPORTING, STORING AND CYROPRESERVING BODY FLUIDS

(75) Inventor: Eberhard F. Lampeter, Leipzig (DE)

(73) Assignee: Vita 34 AG, Leipzig (DE)

( * ) Notice: Subject to any disclaimer, the term of this patent is extended or adjusted under 35 U.S.C. 154(b) by 485 days.

(21) Appl. No.: 10/854,622

(22) Filed: May 26, 2004

(65) Prior Publication Data

US 2005/0084838 A1   Apr. 21, 2005

Related U.S. Application Data

(63) Continuation-in-part of application No. 10/473,094, filed as application No. PCT/EP02/11564 on Oct. 16, 2002, now Pat. No. 7,618,584.

(30) Foreign Application Priority Data

Oct. 22, 2001   (DE) ................. 101 51 343

(51) Int. Cl.
*A61B 19/00*   (2006.01)
(52) U.S. Cl. ............... 604/410; 604/408; 600/573
(58) Field of Classification Search ............... 604/6.15, 604/6.16, 403, 408, 410; 220/501; 383/210, 383/42, 38; 435/284.1, 325, 372, 374; 600/573, 600/580; 422/44
See application file for complete search history.

(56) References Cited

U.S. PATENT DOCUMENTS

| | | | | |
|---|---|---|---|---|
| 5,217,627 A | * | 6/1993 | Pall et al. ............. | 210/767 |
| RE35,804 E | * | 5/1998 | Stewart ............... | 210/767 |
| 5,879,318 A | | 3/1999 | Van DerHeiden et al. | |
| 5,928,214 A | * | 7/1999 | Rubinstein et al. ...... | 604/410 |
| 6,059,968 A | * | 5/2000 | Wolf, Jr. ............. | 210/252 |
| 6,328,726 B1 | * | 12/2001 | Ishida et al. ........... | 604/408 |
| 2005/0274673 A1 | * | 12/2005 | Corbin et al. ........... | 210/645 |

OTHER PUBLICATIONS

Pall-Gelman Catalog, p. 63 (2000).*
Lampeter, E., CE Documentation, Technical Dossier, VITA 34, "Closed System for Collection, Processing and Storage of Cord Blood," Hegewald Medizinprodukte GmbH, Jan. 2003.

* cited by examiner

*Primary Examiner*—Leslie R Deak
(74) *Attorney, Agent, or Firm*—Montgomery, McCracken, Walker & Rhoads, LLP; Evelyn H. McConathy

(57) ABSTRACT

The present invention provides a method for expanding a pre-assembled closed, sterile container system used for the collection, transportation, storage and cryopreservation of biological fluids, such as, blood, bone marrow or umbilical cord blood. The closed sterile bag system comprises a plurality of parts including inlet and or outlet elements and regions for mixing and storing body fluids and cryopreservation liquids, wherein connecting lines provide sterile connection of each component, and wherein the parts are hermetically sealable and separable to maintain sterility system. The methods herein further provide a means for introducing fluids into and/or extracting fluids from a pre-assembled, closed, sterile container system, while maintaining a closed, sterile system without the need to operate under ultra-clean room conditions.

14 Claims, 10 Drawing Sheets

STERILE SYSTEM AND METHODS FOR COLLECTING, TRANSPORTING, STORING AND CYROPRESERVING BODY FLUIDS

REFERENCE TO RELATED APPLICATIONS

This application is a continuation-in-part of U.S. application Ser. No. 10/473,094, filed Sep. 25, 2003, now U.S. Pat. No. 7,618,584 and claims priority to PCT Application No. PCT/EP02/11564, filed Oct. 16, 2002, which also claims priority to DE 101 51 343.7, filed Oct. 22, 2001, each of which is herein incorporated by reference in its entirety.

FIELD OF THE INVENTION

The invention relates to the cryopreservation of body fluids. More specifically, the present invention relates to a system and method of preparing, transporting, processing, storing and cryopreserving body fluids.

BACKGROUND OF THE INVENTION

The cryopreservation of body fluids, such as, peripheral blood, bone marrow and umbilical cord blood, including hematopoetic stem cells and other cells contained therein, has assumed immense commercial significance as the development in human medicine has progressed. Umbilical cord blood and its preservation over a number of years, known as long-term preservation, are crucially significant in connection with possible later treatment of a child, youngster or adult with means based on the body's own substances, for example, in the situation of a transplant. However, this valuable blood is available only at the birth of the child. After the umbilical cord has been cut, it still contains blood that is no longer required for the child.

In the case in which long-term preservation is intended, this blood, often an amount of blood with a volume of about 50 to 100 ml, is collected and prepared for cryopreservation and subsequently frozen by known methods. The aforementioned small amounts of blood removed must expediently be frozen and stored in such a way that a number of samples can be examined and used independently and at different times from one another, possibly several years apart, by the latest methods then available. Without knowledge, today, of the methods that may be applied in the future, cryopreservation of all constituents of the body fluid removed is considered appropriate.

Currently, separate open systems are used commercially for the preparation and freezing of the body fluids (Macropharma, Fresenius, Baxter), and require processing under sterile benches (clean room classes A and B) in a hospital or laboratory. Usually several individual containers or bags are used, requiring the transfer of fluid contents into other bags during processing after the original collection bag is opened. For instance, the umbilical cord blood is collected by a system which often comprises one or more removal cannulas, one or two containers which contain citrate, and the actual blood collecting container. The aforementioned parts of the system are connected in a communicating manner to one another by flexible tubes. Such a system is known in the prior art, for example from U.S. Pat. No. 5,879,318. However, such systems require the use of expensive ultra-clean rooms and many clinical centers use their own, non-standardized procedures for the processing of biological fluids, tissue, bone marrow or stem cells prior to freezing and storage. Consequently, such procedures carry a high risk of contamination of the cryopreserved preparation, particularly stem cell contents.

Following the preparation of the blood, decanting then takes place from one system into another for the purpose of cryopreservation. Thus the body fluids are moved from a sterile container into a sterile freezing container, which often has to be performed under ultra-clean room conditions. Often high expenditures are required to meet the statutory predetermined ultra-clean room conditions with respect to human medicine, such as, the requirements according to GMP. These sterile conditions and requirements for collecting body fluids in sterile form and preparing them for cryopreservation usually cannot be provided in every delivery ward or medical facility.

Accordingly, until the present invention, the preparation for cryopreservation of umbilical cord blood always took place by the following steps: 1) removing the blood from the umbilical cord and introducing it into the transporting bag, 2) adding citrate or preservative, unless already provided in the bag, 3) closing the bag and transporting the filled bag at room temperature to an ultra-clean room (necessarily within about 24 to 48 hours), and 4) transferring the blood and added cryoprotectant from the transporting bag into a sterile freezing bag under ultra-clean room conditions. Moreover, current processes require at least two separate systems—one for collection of the body fluids, such as the umbilical cord blood, and one for freezing the collected fluids.

Consequently, a need has remained for an expandable system and method for the collection, processing and cryopreservation of biological fluids and cells contained therein, that meet the sterile requirements for human medicine under normal hygienic laboratory conditions, without the need for the use of an expensive ultra-clean room, and without a need for dual or multiple independent systems for each step.

SUMMARY OF THE INVENTION

It is an object of the invention to provide an expandable system and methods that reduce the costs of collecting, handling, storing and cryopreserving one or more body fluids, wherein such system and methods further allow for the easy and safe manual handling, while ensuring that the requirements for sterility in human medicine are met. Preferably, the system is a bag system for cryopreservation that will permit the addition of additional components and/or sterile fluids to the system without breaching the sterility of the closed system, and without the need for ultra-clean room conditions. Furthermore, it is an object of the invention to provide a method of preparing body fluids, such as peripheral blood, bone marrow and umbilical cord blood, for long-term storage by cryopreservation using such transporting and storing system. Yet another object of the invention is to provide a method of introducing one or more additional fluids, reagents or mixtures to an assembled and sealed bag system, or removing same from the system, while maintaining a closed, sterile system under normal hygienic conditions, without the need for ultra-clean conditions.

It is a preferred object of the invention to provide a bag system, wherein the bag system comprises additional regions for storing a mixture of liquids and the collected body fluid, and wherein the regions are hermetically sealable and separable from one another and which are connected in a communicating manner to one another by connecting lines, such that the system as a whole is a closed, sterile system, even after additional components are added.

It is also an object of the invention to provide a method for handling body fluids in which the parts of a transporting and storing system, which are connected in a liquid-communicating manner to one another, form a closed, sterile system, before body fluids are introduced into the transporting and storing system. Thus, the preferred methods rely upon the fact that the region or the regions for storing a mixture of liquids and the body fluids are hermetically sealable and separable from one another, permitting the system to be expanded or reduced without adversely affecting the sterility of the system as a whole or of the biological fluids contained therein. In such methods, body fluids, such as blood, bone marrow or umbilical cord blood are collected, transported and stored under sterile conditions permitting viability of cells within such fluids to remain viable. Preferably, the valuable biological fluids are from a mammal or other animal, and more preferably the mammal is human. Use of the methods is, therefore, also suitable in principle for other human or animal tissue or body fluids. In principle, the method can also be applied if, instead of bags, the expandable transporting and storing system uses other known liquid storage elements known for acceptable use in medical and laboratory technology, such as bottles or other shaped containers. In this case, it is expedient to use customary means, such as pumps, at least for part of the liquid communication in the transporting and storing container. It is particularly economical in terms of the preferred methods that easy and consequently low-cost freezing is possible using conventional equipment for cryopreservation.

Another object of the invention is also achieved by a method of introducing one or more fluids or fluid mixtures into the closed bag system after the bag system is assembled. In accordance with the bag system of the present invention, the parts of the transporting and storing bag system form a closed system before the body fluid is introduced. In a preferred embodiment of the bag system of the present invention, inlet elements comprising a sterile filter are provided for adding body fluids and liquids into the transporting and storing system. These inlet elements are connected in a liquid-communicating manner to the other components of the system during the assembly of the system and are integral with the closed, sterile system. However, in order to combine the commercially available components to form a closed, sterile system, the bag system is assembled under ultra-clean room conditions.

Access to the closed, sterile transporting and/or storage systems utilize a variety of known elements, such as, but without limitation, a pre-existing port, such as, a rubber septum is provided that is integral to the bag or storage container. In other embodied systems, a glass ampoule with a pierceable stopper is provided that is integral to the storage container. In such systems, in order to add or drain fluid from the closed system, a needle or syringe punctures the port to access the bag, storage container or ampoule. The port or septum returns to a closed position once the syringe is extracted. Accordingly, the ability to introduce an additional fluid to the embodied systems, while maintaining a closed, sterile environment, requires assembly of the closed system, such that pre-existing inlet elements or ports are put into place. Without such pre-existing inlet elements or sterile ports, no sterile connection exists to add fluid to the system after the system has been assembled under the ultra-clean room conditions. Thus, it is a particular object of the present invention to provide a method for introducing one or more fluids to the closed, sterile system after the bag system has been assembled, by the addition of an expanding second sterile bag system, or using such second bag system to remove one or more fluids from the expanded system, such that in either case no ultra-clean room conditions or use of pre-existing inlets or ports are further required.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE DRAWINGS

The foregoing summary, as well as the following detailed description of the invention, will be better understood when read in conjunction with the appended drawings. It should be understood, however, that the invention is not limited to the precise arrangements and instrumentalities shown.

DETAILED DESCRIPTION OF PREFERRED EMBODIMENTS

Figure 1:
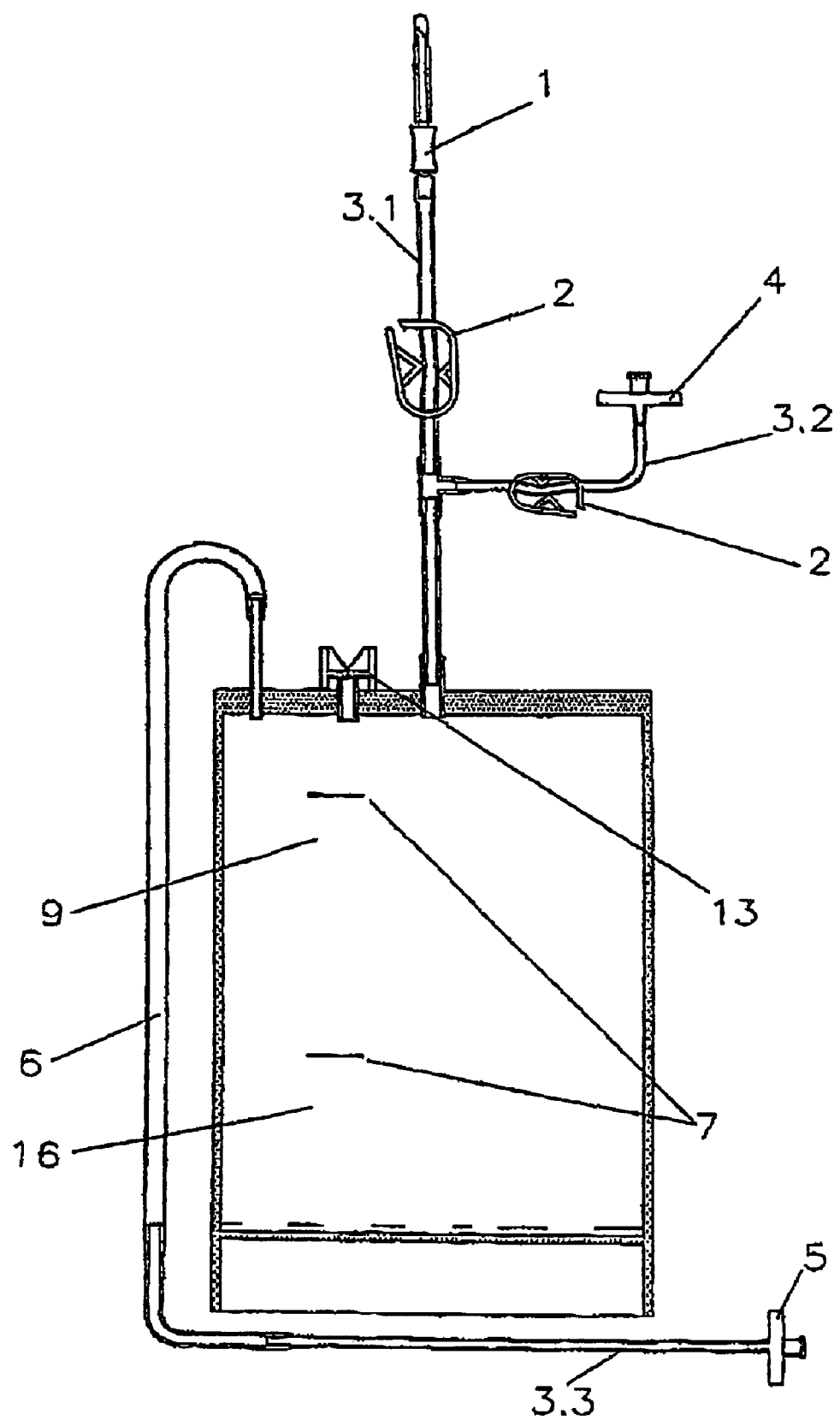
FIG. 1 shows an embodiment of the bag system of the present invention, having a mixing and freezing bag 16.

The invention provides an expandable collection, transportation and storage system in the form of a "closed" sterile system, at least at the time when a body fluid is introduced into the system, particularly when introduced directly from the human body. Consequently, optimum sterility is achieved during use for collecting, transporting, storing and cryopreserving the body fluid, and even for delivery of the cryopreserved fluid for a later use, such as delivery of the fluid to a transplant surgeon. Regions for mixing the liquids with the body fluid and/or for storage are, for the purposes of the invention, all known closable liquid storage containers, such as, for example, but without limitation, containers and bags of medical and laboratory technology which are formed in such a way as to be liquid-tight with respect to the atmosphere. Bags are preferred in the present invention, and it will be referred to as a bag system, although it is intended to also be adaptable to other containers. The term "cryopreservation" as used herein is intended to include known cryopreservation techniques, as well as vitrification techniques, and the temperatures and exposure times associated with storing viable cells by those techniques, while retaining an acceptable level of viability.

The system is designed so that it is possible to separate those parts of the bag system that are no longer required from the remainder of the system, in particular for cryopreservation purposes. The parts that are no longer required for expedient handling, such as, for example, the device for taking up the body fluid after transferring the body fluid into a region for mixing, are separable from the remainder of the bag system without opening the closed system. At the time of freezing, the closed system then only comprises parts which are separated and hermetically sealed from one another, and are no longer connected in a communicating manner to one another. This results in a savings of transportation and storage costs.

In a preferred embodiment of the invention, the regions for storing the mixture of liquids, to permit and/or assist the cryopreservation and the transferring of the body fluid, are hermetically sealable and separable from one another, thereby making it possible to separate the total amount of the aforementioned mixture into a number of part-amounts, which are separable from one another, as desired with respect to size or volume. The separated part-amounts are available in particular after freezing for bacteriological and serological examinations and for monitoring the long-term storage, without a need for opening the sealed, complete bag system (all parts are sterile and pyrogen-free at the time the system is sealed). The entire handling in the laboratory, for example, adding a cryoprotectant (or cryopreservative) via a sterile filter, can therefore be performed under normal hygienic conditions (for example clean room class D). Ultra-clean room conditions are not required for use of the embodied bag system of the present invention.

The materials used for the components of the bag system are known in the art, and are selected and adapted to one another in a known manner. Materials used in components of the system have been tested and proven to be biocompatible (meeting FDA Guidelines G95-1 for long-term exposure (>30 days) with circulating blood), non-thrombogenic and non-hemolytic. For example, the materials are selected in part based upon the type of the medium or media with which it comes into contact, the exposure time to the medium, the type and manner of the sterilization and the temperature ranges, i.e., particularly the maximum and minimum temperature to be encountered during handling and freezing.

Recognizing that alternatives are available at each step, the following production methods are used to prepare a preferred embodiment of the bag system of the invention (see, e.g., as described in CE Documentation, Technical Dossier, Hegewald Medizinprodukte BmbH, January 2003). The production of the bags is performed in clean rooms (class 100.000). The empty bags are produced from lay-flat material of poly-(vinyl) chloride (PVC) transparent film or lay-flat tubing material of polyurethane, as well as small tubes of both materials. The empty bags are manufactured by cutting the tubular film to size. The small tubes for filling and/or delivery are assembled to the bags using a high frequency welding machine. Bags are assembled and connectors are joined to the tubes using adhesives (e.g., cyclohexanone). In the case of the PVC bags, before welding the bags are printed by means of a hot-printing process before welding. DMSO filter is assembled to the storage bag by means of a UV curing adhesive. The bag systems are packaged in PA/PE primary packaging and sterilization bags (Gruber Foils, Germany). After packaging the bags are ethylene oxide (ETO) sterilized.

In a preferred embodiment, but without intended limitation, the collected biological fluid is delivered from the collection device to a sterile collection bag, which may be the mixing bag or in some instances depicted herein, there may only be a single mixing/freezing bag. The bag is made from a standard foil sealed with sterile tubings that are connected with a filter for DMSO, sampling bag (PVC) and a puncturing line with a pre-sterilized cannula. The bag used for receiving the biological fluids from the collection device may be made from a foil manufactured from standard PVC material (Draka Solmed 3224, Solvay Draka B.V., Enkhuizen, Netherlands) that meets the requirements of Pharm. Euro. $3^{rd}$ ed., §3.1.1.1. "Materials based on plasticized poly-(vinyl chloride) for containers for human blood and blood components"). No other additives are used in the manufacturing of the foil material.

Tubing may be made from standard PVC material (Draka Solmed 3227 and 3267, Solvay Draka, that meet the requirements of Pharm. Euro. $3^{rd}$ ed., §3.1.1.1, as above). No other additives are required in the manufacturing of the tubing material. Part of the tubings comprises connectors (e.g., T-connector and tubing connector). Both components may be made from PVC type G.60.0.0.025.74 (Rottolin-Werk Julius Rotter & Co., Bayreuth, Germany) and PVC 3222 (Draka Solmed, Solvay Draka). Known plastics that meet the aforementioned requirements and are authorized for applications in human medicine are particularly useful for the present invention.

The cannula used in the disclosed embodiment are manufactured by SFM GmbH (Waechtersbach, Germany), using standard materials, such as polycarbonate Makrolon 2858 and stainless steel 1.4301. The cannula are coated with silicone AK12500. The cap is made from Vestamid (Degussa, Germany).

Liquids that permit and/or assist the cryopreservation, for the purposes of the invention, include those known in the art for such purposes, and may include yet to be discovered media for cryopreservation or vitrification, or for preparation for cryopreservation or vitrification of body fluids. For the cryopreservation of blood, such liquids include, for example, but without limitation, liquid media for preventing blood coagulation (anticoagulant), such as, citrate phosphate dextrose (CPD), or for thinning blood, such as sodium chloride solutions, and cryoprotectants or cryopreservative solutions (also referred to as cryopreservatives), such as dimethyl sulfoxide (DMSO). The CPD solution for the collection bag is delivered in a sterile bottle/container and released after incoming inspection tests. Aseptic filling is performed in a Class A environment under LF, using pre-sterilized equipment into the ETO-sterilized empty bag systems. The collection bag is then closed using a connector. No solvent adhesives are used.

After filling the products are packed in a presterilized transparent primary PA/PE bag under LF conditions. Product quality is intensively monitored during manufacture by means of regular in-process controls. This ensures that the quality, functioning capability and safety of the end product are optimal. Aseptic filling is validated according to ISO 13408 and complies with the relevant international standards. Thus, the bags systems are produced under controlled conditions in a reproducible way.

In a preferred configuration according to the invention, the regions for storing the mixture of liquids and the body fluid are configured in such a way that there are at least two chambers of a bag. Two chambers permit the separation of two part-amounts of the liquid mixture to be stored, so that a subdivision is possible, which is also expedient for practical purposes with respect to the total amount of the liquid to be stored. Thus, material for the bags is selected which can be sealed and divided into chambers. The use of a bag having flexible walls is particularly advantageous if the handling is carried out manually by midwives or medical personnel. Such flexible walled bags are well known in, for example, the arts of blood banking, transfusion and intravenous preparations. Exposure of the flexible walls to manual pressure and the use of gravity have the effect of transporting the liquid and gas within the bag system and of bringing about thorough internal mixing.

In a preferred embodiment of the invention the bag system is configured so that a region for storing the mixture of liquids and the body fluid further comprises a connecting line, which preferably has a number of segments, permitting the segments to be hermetically sealed and separated from one another. This configuration achieves the effect that smaller part-amounts, which serve in particular as samples for monitoring long-term preservation, are separated in a simple manner from one another. For example, the segment may be hermetically sealed by means of welding the flexible and transparent connecting line which is arranged between the freezing bag and the mixing bag, or between the freezing bag and the sterile filter used for venting.

In certain preferred embodiments of the invention a filling-level indicator is advantageously placed in the respective region for mixing the liquids. For transparent bags, the filling-level indicator may take the form of applied corresponding markings printed onto the inner or outer wall of the bag (printing on the outer wall is preferred to avoid risk of contamination of the cryopreserved fluids if the print separates from the inner surface of the bag). This is particularly useful to indicate the minimum filling height for the body fluid introduced into the bag and the set filling height, which is achieved after filling with the thinning liquid, and permits monitored of the levels.

Such printing on bags is well known in the blood banking and intravenous product fields. In a preferred embodiment, the printing dyes for the bags are pharmaceutical hot stamp dyes (type SV) on a dry polyester carrier. The dyes contain organic and or inorganic pigments and binding agents. Such a product has been developed specifically for medical applications and are tested according to USP Class VI. The material is considered to be non-toxic, and comply with the requirements of surface coatings, as specified in EN 71, Part 3, 1994.

In connection with long-term preservation, it is also advantageous that in certain embodiments the regions for storing the mixture of liquids and the body fluid, which have been separated from the remainder of the system, are surrounded by an enclosure. For example, in an embodiment of the invention, the enclosure is a transparent orange overwrapping, like a second bag covering the whole storage part of the bag system. The enclosure is transparent to permit checking the label on the actual sample bag contained therein. It may be made, e.g., from Kapton (Teflon) or similar durable material, and is intended to stay on to provide protection for the stored portion(s) of the bag system throughout the entire storage period, although in an alternative embodiment it may be retained for only selected storage times. It is designed to be removed just before use of the stored cryopreserved biological material, and is not intended to be reusable for other specimens, although if reused, the enclosure is contemplated as part of the present invention. Thus, the enclosure serves in particular for mechanical protection and may additionally ensure gas-tight and liquid-tight enclosure of the stored bag system and contents contained therein.

It is preferred that the bag system is intended for single use purposes only. Thus, materials and design of the system are selected for such single use purposes. Disposable systems, and parts used therein, have a range of known advantages, based upon the knowledge that they will be used only once, and possibly used only briefly. For example, the device for collecting the body fluids, may be manufactured inexpensively from medically suitable materials, so long as the finished product complies with the sealable, sterile characteristics of the non-hemolytic, non-thrombogenic, and non-pyrogenic system.

Because the bag system of the present invention utilizes fewer parts than previously used collection or transport systems, it is less expensive and permits easier handling. For example, components may be selected for a single mixing and freezing chamber, whenever it is ensured that freezing of the collected fluids will begin within a relatively short time, i.e. within 10 to 20 minutes, after the body fluid has been taken up into the bag system. Alternatively, the bag system according to a preferred embodiment is configured so that the region for mixing the liquids with the body fluid is arranged to form a mixing bag, and the region for storing the mixture of liquids and body fluid is arranged in a freezing bag, wherein the freezing bag has, for example one or two freezing chambers, or a reasonable number more as needed.

The freezing bag (or mixing and freezing bag if only one bag is used) may in a preferred embodiment be made from a foil material that is a polyether-based aromatic polyurethane type PUR 2541 (e.g., Tecothane, having high solvent resistance and resistance to DMSO, and manufactured by Thermedics Polymer Products (Wilmington, Me.). Tubings that are attached to the polyurethane bag are made from polyether-based aromatic polyurethane type PUR 4741 made by Thermedics. Connections can use model 3900 Sterile Tubing Connectors (SEBRA, Tuscon, Ariz.). The twist-off connectors attached to the bag are made from PUR 2741.

The use of a multiple bags, e.g., at least one for mixing and one for storing, which may consist of different materials, results in better handling, and consequently enhanced functional dependability by eliminating subjective manipulation errors. For example, specific material selection makes it possible in the case of a bag system for umbilical cord blood to provide CPD already in the mixing bag at the time the complete bag system is being assembled under ultra-clean conditions. Thus, there is no longer any need for independent sterile introduction of CPD (which is itself sterile), or alternative anticoagulant material, into the bag system immediately before the umbilical cord blood is taken up in the delivery room. CPD typically contains sodium citrate×2 $H_2O$ (26:30 g/l), citric acid×$H_2O$ (3:27 g/l), $NaH_2PO_4$×2 $H_2O$ (2:51 g/l), glucose×$H_2O$ (25:50 g/l) and water for injection (raw materials meet Pharm. Eur. Monograph 209 requirements, and is provided in aseptically filled containers by licensed pharmaceutical manufacturers, e.g., Biochrom AG, Berlin, Germany).

It is also, therefore, possible to delay freezing of the collected fluids for up to about 20 hours (up to 48 hours in some cases) after collection of the blood into the bag system without significant damage to constituents of the blood. However, the timing of the use of the bag system or delays before cryopreservation, is relative to the fluid being collected, not to the present invention. This permits intermediate storage at room temperature before freezing.

The selection of the material for the freezing bag of such an embodiment is primarily determined by its temperature resistance with respect to the actual cryopreservation (temperatures down to about −196° C.). Sterilization by autoclaving is, consequently, often ruled out. As noted above, however, sterilization by ETO, gamma radiation or other non-temperature sensitive methods is permitted.

Blood or umbilical cord blood has a tendency to foam, in particular during mixing with other liquids. As a result, air bubbles are trapped in the liquid or in the liquid mixture, with the result that a liquid-air mixture is produced. However, it is essential that the mixture of liquids, which permit and/or assist the cryopreservation and the body fluid, be transferred virtually without any bubbles into the storage region of the system. Freedom from bubbles is an important criterion for the quality and, consequently, the suitability for the intended use of the biological fluid that is being stored. Captured air bubbles will collapse at very low temperatures, thereby creating negative pressure in the bag when it is already fragile due to the low temperatures. Oxygen in the air bubbles becomes liquid at −160° C., while the optimal storage temperature of the biological fluids in the system is −190° C. Thus, the volume and pressure of an air bubble within the system will be significantly reduced during the freezing process, and may cause the plastic of the bag to crack. To remedy this effect, for example, an arrangement of an outlet element and/or of the corresponding connecting lines is included in the system, so that manual manipulation can be performed until the liquid mixture is virtually free from bubbles.

In an embodiment intended to minimize or eliminate the aforementioned air-liquid problem, the bag system is designed having two bags for mixing and storing, wherein preferably the mixing bag and the freezing bag are connected to each other by two connecting lines. With this type of arrangement, i.e. a closed circuit between the two bags, the liquid-air mixture contained in the bag system can be manipulated in such a way that there are no or minimal inclusions of air in the liquid at the time of freezing in that amount of liquid located in the region(s) of the system intended for storage. The mixing bag and the storage bag are connected by two lines—one for blood transfer, while the other has an outlet to release air and air bubbles from the storage bag.

Alternatively, in another embodiment the mixing bag and the freezing bag are connected to each other by a connecting line. This configuration expediently requires the arrangement of an outlet element on the freezing bag, for example a sterile filter, which permits venting of air from the bag system. Such a filter would allow air-flow in both directions, and air may be pressed out by squeezing the bag, but entry of contaminating microorganisms and bacteria is prevented. Thus, the system remains sterile.

Reference is now made to the accompanying Figures for the purpose of describing in detail, preferred embodiments of the present invention. Like elements have the same numbers throughout the several views, and in general are as follows: inlet device 1 for the collection of body fluid into the system; shut-off elements 2; connecting lines 3; inlet element 4; outlet element 5; segments 6; fill-level indicator 7; enclosure 8; mixing and freezing chamber 9; freezing chamber 10; mixing bag 11; freezing bag 12; removal adapter 13; bag with A 14; bag with B 15; mixing and freezing bag 16; protective bag 17; glass ampoule 18; liquid for avoiding blood coagulation A; liquid for thinning B; cryoprotectant or cryopreservative C; liquid mixture of collected and added liquid components D; connection assembly 20; sterile filter 22; connection tube 23; collection bag 26; processing or separation bag 27 and sterile connectors SC. However, the detailed description accompanying each Figure is not intended to limit the scope of the claims appended hereto.

FIG. 1 shows an embodiment of the bag system with a mixing and freezing bag 16, which is connected in a communicating manner by three connecting lines 3.1, 3.2 and 3.3, to a collection device 1 for the direct collection of umbilical cord blood, an inlet element 4 and an outlet element 5. Removal adapter 13 permits the sterile removal of the transported or stored liquid contents of the bag. The communication, i.e., in particular the liquid transport and the air exchange, between the aforementioned parts of the bag system is realized by opening or closing of the shut-off elements 2, which may take the form of commercially available hose clips. The transport of the liquid media, possibly with air inclusions, is realized in the bag system by using gravity and by exertion of manual pressure on the flexible walls of the bags. The inlet element 4, which as shown in FIG. 1, is a sterile filter, serves for the sterile introduction of the liquids which permit and/or assist cryopreservation, i.e., in particular a liquid for inhibiting or preventing blood coagulation (A), a liquid for thinning (B) and/or liquid cryoprotectant (C). Note that the liquids added to the various bags are determined by the body fluid being collected and how it is to be handled, used and preserved. Thus, the additional liquids themselves, as well as their selection are not part of the invention. Only the ability to provide such liquids within the system in a sterile and efficient manner is provided.

After the introduction of the umbilical cord blood and/or liquids which permit and/or assist cryopreservation, the connecting lines 3.1 and 3.2, which consist of a plasticized PVC material, can be hermetically sealed and/or separated from the remainder of the system by welding, for example with a transportable film welding appliance. Like connecting lines 3, flexible mixing and freezing bag 16 preferably consists substantially of a flexible plastic material, i.e., ethylene vinyl acetate (EVA), which is temperature-resistant at least down to a temperature of −196° C. and can be sterilized by radiation sterilization (gamma radiation).

On transparent freezing bag 16, which is designed, for example in an exemplary method, to hold a maximum fluid volume of 180 ml, there is fill-level indicator 7. The indicator indicates the values or amounts for the filling, for example in an exemplary method, a minimum filling amount would be 60 ml and the set filling amount would be 160 ml. Either a measurement scale or range can be provided by the indicator, so that various fill levels can be selected, or in the alternative, set levels such as for the minimum and filled point only can be shown, or in yet another alternative, words can be added to indicate to the user of a provided measurement scale, for example, where the set points would be. Indicator 7, although it may not be expressly described may appear on any bag in the following figures or in any embodiment in which measurement of the bag contents is useful.

Arranged on mixing and freezing bag 16 is removal adapter 13, which permits the sterile removal of the stored liquid mixture. Connecting line 3.3 is connected to outlet element 5, which is a sterile filter and preferably serves for air discharge from the bag system.

The thin-walled, flexible and transparent connecting line 3.3 is also a region for storing the mixture of liquids and the body fluid. The line is dividable into segments 6, for example in an exemplary system, five such segments, with a capacity of in each case about 1 ml, which are hermetically sealable and separable from one another and the remainder of the system (not shown in FIG. 1). Segments 6 can be produced by welding, for example with a transportable film welding appliance, to separate one segment 6 from the remainder of, for example, connecting line 3.3 (see additional description of segments 6 in FIG. 8).

The joining together of the previously sterilized parts of the bag system, which comprise commercially available parts and components, to form the closed system for the purposes of the invention, is performed under ultra-clean room conditions. However, once the system of the invention is formed and sealed closed, ultra-clean room conditions are no longer required for managing or handling the collected body fluids. Welding, adhesive bonding and known joining techniques authorized for human medicine can be used for the joining together the bag system components.

Figure 2:
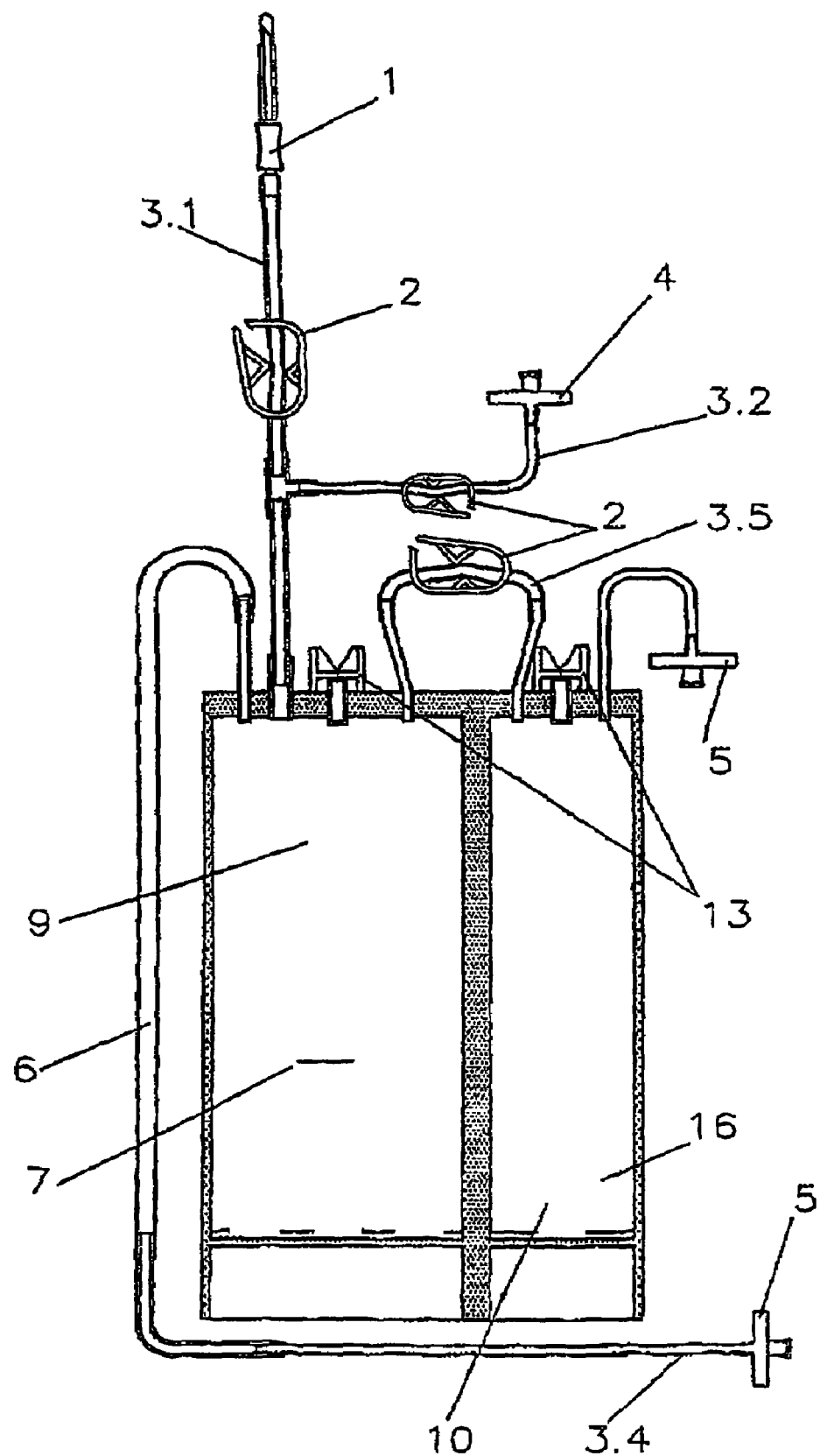
FIG. 2 shows an embodiment of the bag system, having a mixing and freezing bag 16, wherein there are two chambers: a mixing and freezing chamber 9, and a freezing chamber 10.

For certain applications it is advantageous that the region for mixing the liquids with the body fluid and the region for storing the mixture of liquids and body fluid are arranged in mixing and freezing bag 16. The embodied bag system represented in FIG. 2 shows mixing and freezing bag 16, which has mixing and freezing chamber 9 and freezing chamber 10, which are connected in a communicating manner to each other. Mixing and freezing bag 16 communicates via a number of connecting lines 3 with a device 1 for the direct collection of umbilical cord blood, an inlet element 4 and two outlet elements 5. The two chambers, which can be separated from each other, that is mixing and freezing chamber 9 and freezing chamber 10, in each case have a removal adapter 13 and an outlet element 5.

Figure 3:
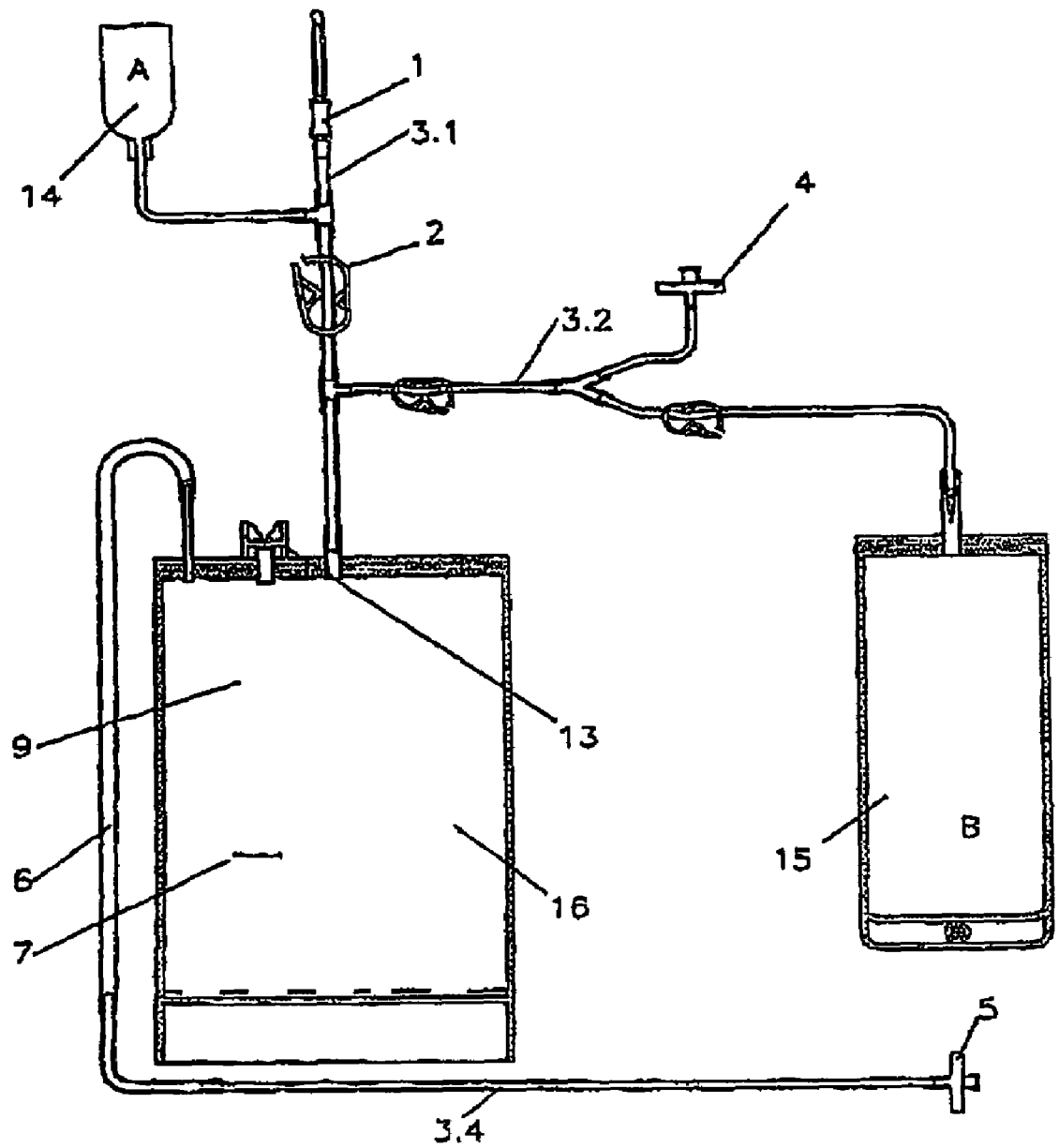
FIG. 3 shows an embodiment of the bag system, having a mixing and freezing bag 16, wherein there is a mixing and freezing chamber 9, a bag containing a liquid A for avoiding blood coagulation 14, and a sodium chloride B bag 15.

FIG. 3 shows a different embodiment of the bag system, having a mixing and freezing bag 16, wherein there is a mixing and freezing chamber 9. The configuration presented in FIG. 3 differs from FIG. 1, in that it further includes bag 14, which in an exemplary method contains 21 ml of CPD, for avoiding blood coagulation (A), and bag 15, which in an exemplary method contains 100 ml of a sodium chloride solution (NaCl) (B) for isotonicity. Mixing and freezing chamber 9 has a removal adapter 13, which permits the sterile removal of the transported or stored liquid contents of the chamber. The bags are, respectively, connected to the closed bag system via connecting line 3.1 and 3.2. The bags 14 and 15 have, in each case, with respect to the connecting lines 3.1 and 3.2, an interruption valve (shut off element 2), which is a hose clip.

Figure 4:
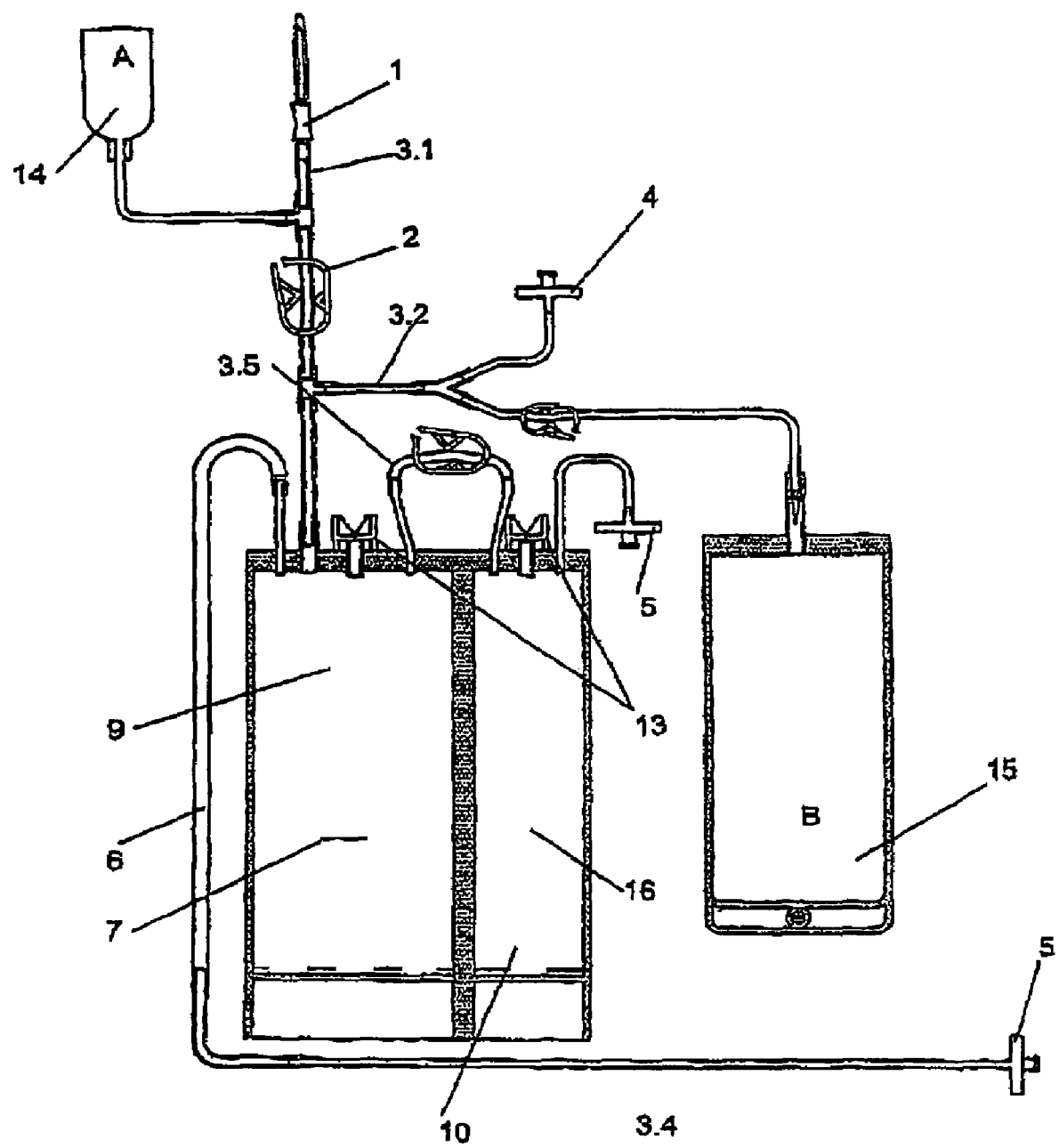
FIG. 4 shows an embodiment of the bag system, having a mixing and freezing bag 16, wherein there are two chambers: a mixing and freezing chamber 9, and a freezing chamber 10, wherein there is also a bag 14 containing a liquid A for avoiding blood coagulation, and a sodium chloride B bag 15.

In FIG. 4, the embodiment of the bag system has a mixing and freezing bag 16, where in a difference from FIG. 3, there are two chambers: a mixing and freezing chamber 9, and a freezing chamber 10. Each chamber 9 and 10 has a removal adapter 13, which permits the sterile removal of the transported or stored liquid contents of the chamber. The embodied system also includes bag 14 containing a liquid A for avoiding blood coagulation, and sodium chloride B bag 15.

Figure 5:
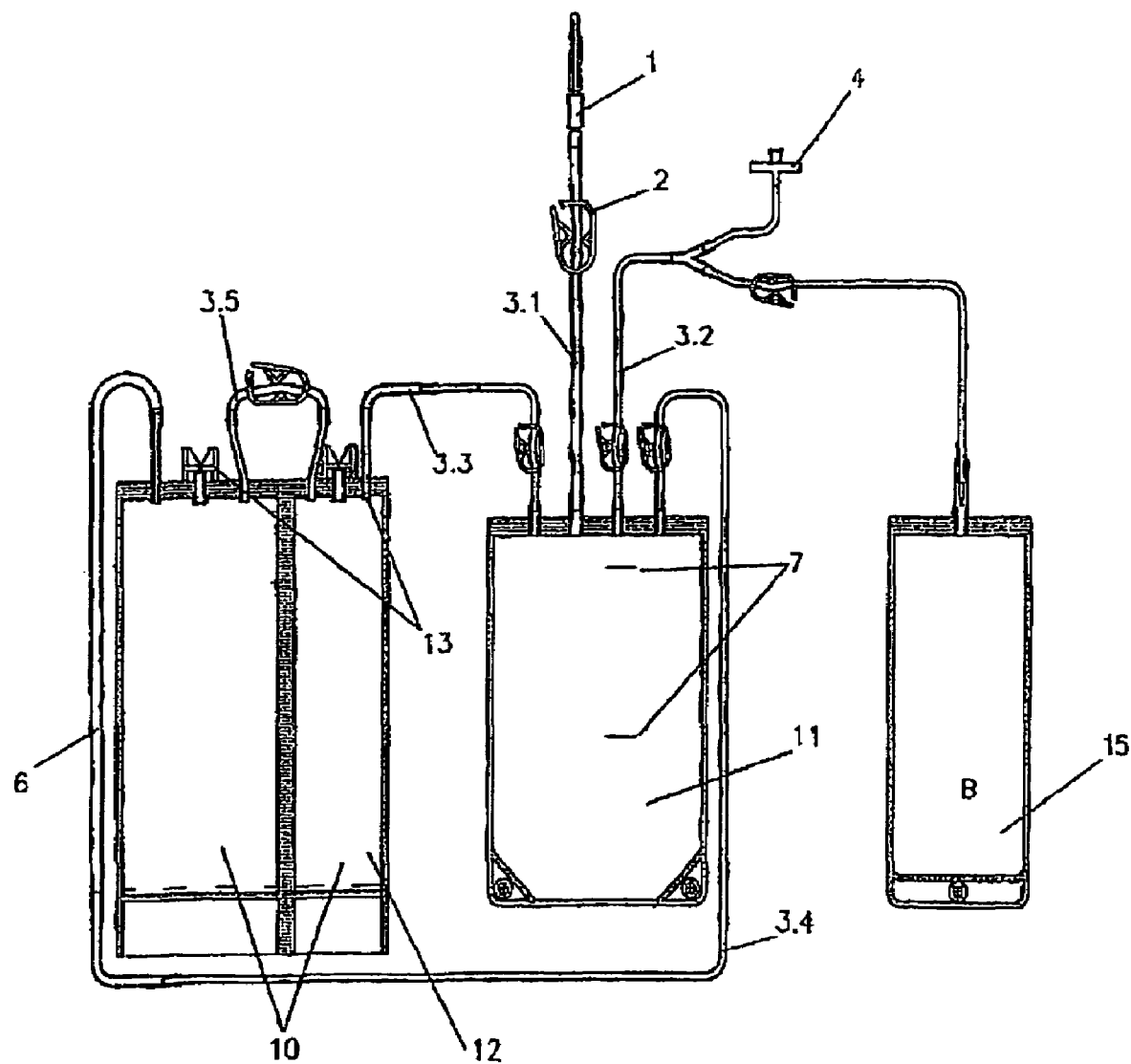
FIG. 5 shows an embodiment of the bag system, having a mixing bag 11 and freezing bag 12, wherein there are two chambers 10, and two connecting lines 3.3 and 3.4 between freezing bag 12 and mixing bag 11, plus a sodium chloride B bag 15.

Represented in FIG. 5 is an embodiment of the bag system having a mixing bag 11, which is connected in a communicating manner by four connecting lines 3.1, 3.2, 3.3 and 3.4 to a device 1 for the direct collection of umbilical cord blood, an inlet element 4, a freezing bag 12 and bag 15 containing solution B. The communication, i.e., in particular the liquid transport and the air exchange, between the aforementioned parts of the bag system is realized by opening or closing the shut-off elements 2. The liquid media, possibly with air inclusions, are mixed, moved and transported into and within the bag system by gravity and by exertion of manual pressure on the flexible walls of the bags. The inlet element 4, which in this configuration is a sterile filter, permits the sterile introduction of a liquid cryoprotectant C, for example DMSO or equivalent cryopreservative.

In accordance with methods provided herein, after the introduction of the umbilical cord blood and/or liquids which permit and/or assist cryopreservation, the connecting lines 3.1 and 3.2 can be hermetically sealed and/or separated from the remainder of the system, by e.g., welding. CPD or equivalent anticoagulant, may be provided in mixing bag 11 as the system is being formed, before the system is sealed closed. Like the cited connecting lines 3, the flexible mixing bag 11 substantially consists of a plasticized PVC plastics material or other equivalent material known in the art for such purposes, which can be sterilized in a way known in the art, e.g., by autoclaving, gamma radiation or the like. On the transparent mixing bag 11, which is designed for a maximum volume of 180 ml, there is a fill-level indicator 7, which indicates at least the values in an exemplary method for the minimum filling amount of 60 ml and the set filling amount of 160 ml.

Freezing bag 12 substantially consists of an EVA plastic material and has two freezing chambers 10, which may be of the same approximate size or of different sizes as shown. The two chambers 10 are connected to each other by connecting line 3.5. Each freezing chamber 10 has a removal adapter 13, which permits the sterile removal of the transported or stored liquid contents of the chamber.

Connecting lines 3.3 and 3.4 connect mixing bag 11 and the chambers 10 of freezing bag 12 to each other. Either one (or both) of the thin-walled, flexible and transparent connecting lines 3.3 or 3.4 may further provide an additional region for storing the mixture of liquids and the collected body fluid in small segments 6. These segments 6, for example five of them, with a capacity of in each case of about 1 ml, are hermetically sealable and separable from one another (not shown in FIG. 5) and from the remaining part of connecting line 3.3 or 3.4. Such seals and separations are produced by welding, for example, with any known and adaptable transparent-film welding appliance (e.g., Composeal, Fresenius Home Care, Bad Homburg, Germany).

The two freezing chambers 10 are connected to each other in a communicating manner by connecting line 3.5. After hermetic sealing and separating of the connecting lines 3.3, 3.4 and 3.5 from mixing bag 11 and freezing bag 12, the two freezing chambers 10 are also separable from each other.

To form the bag system, previously sterilized parts and components of the bag system, which comprise commercially available parts and components, are joined together to form a closed system. For the purposes of the invention, the bag system is initially formed under ultra-clean room conditions. Any welding, adhesive bonding and/or joining techniques that are suitable for the selected materials without damage, and authorized for human medicine, can be used for the joining together (e.g., Composeal, supra).

Figure 6:
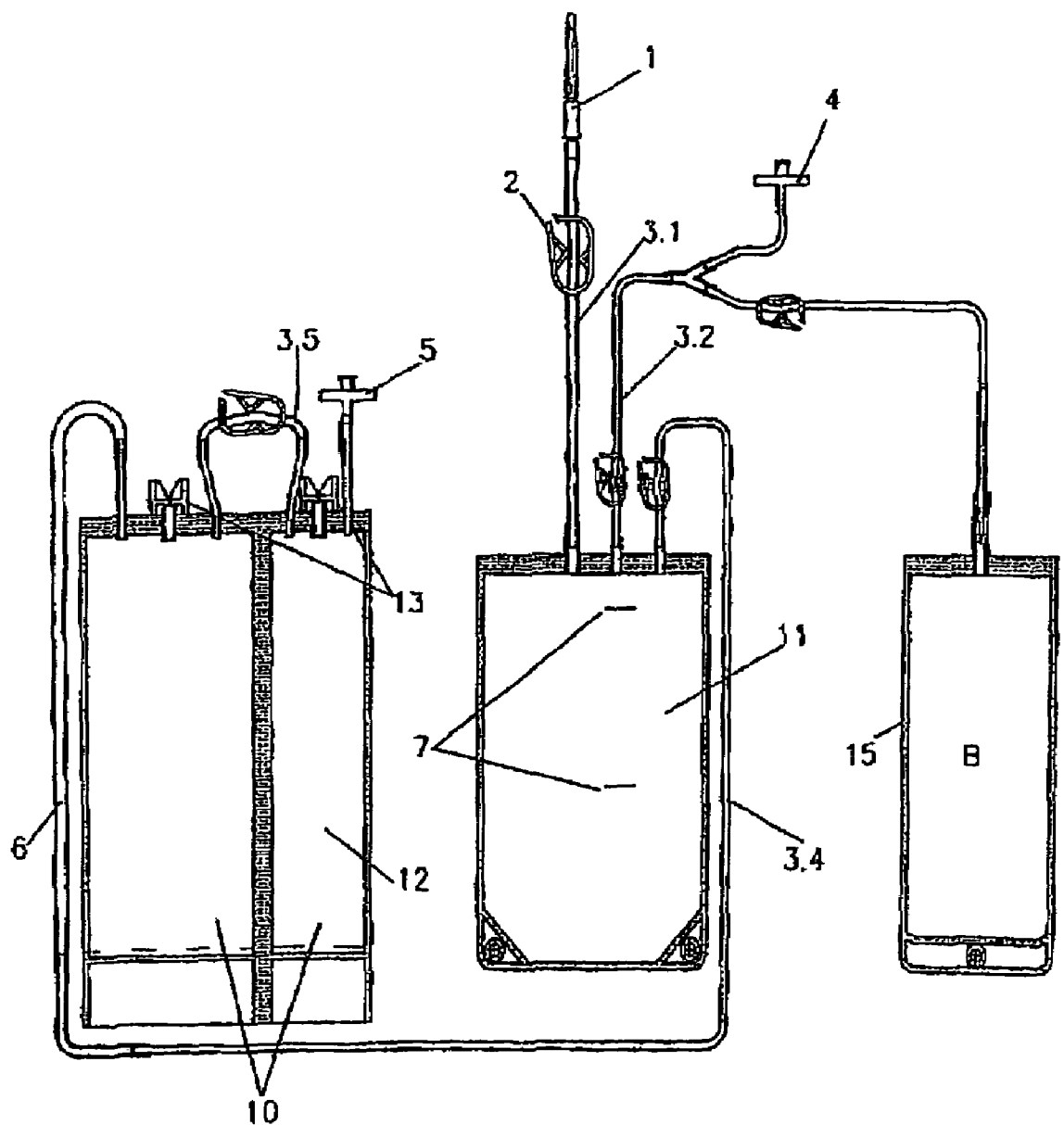
FIG. 6 shows an embodiment of the bag system, having a mixing bag 11 and freezing bag 12, wherein there are two chambers 10, and a single connecting line 3.4 between freezing bag 12 and mixing bag 11, plus a sodium chloride B bag 15.

FIG. 6 shows an embodiment of the bag system, analogous to the embodiment shown in FIG. 5, the FIG. 6 embodiment having a mixing bag 11 and freezing bag 12, wherein freezing bag 12 there are two chambers 10 (connected to each other by connecting line 3.5). One chamber 10 of freezing bag 12 has an outlet valve 5, but the embodied system has only a single connecting line 3.4 between the other chamber 10 of freezing bag 12 and the mixing bag 11. Each freezing chamber 10 has a removal adapter 13, which permits the sterile removal of the transported or stored liquid contents of the chamber. There is also a sodium chloride B bag 15.

A notable difference between the embodiment of FIG. 5 and that of FIG. 6, is the absence in the embodiment in FIG. 6 of connecting line 3.3. Instead of connecting line 3.3, the embodiment of FIG. 6 includes outlet element 5, which is a sterile filter, which particularly serves for venting the system.

Figure 7:
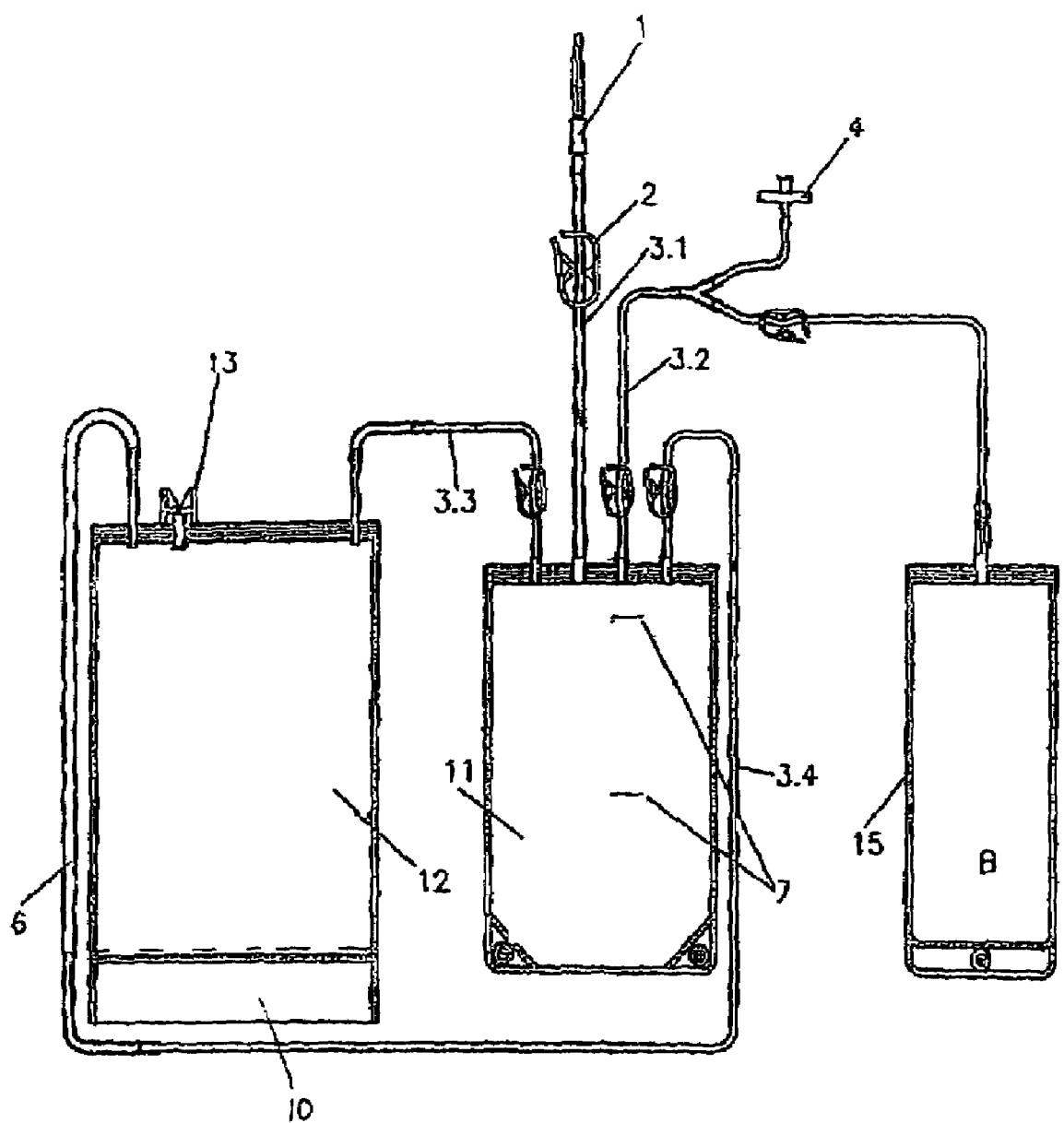
FIG. 7 shows an embodiment of the bag system, having a mixing bag 11 and freezing bag 12, having a single chamber 10, and two connecting lines 3.3 and 3.4 between freezing bag 12 and mixing bag 11, plus a sodium chloride B bag 15.

In FIG. 7, an embodiment of the bag system is shown that is similar to the embodiment of FIG. 5, having a mixing bag 11 and freezing bag 12, and two connecting lines 3.3 and 3.4 between the freezing bag 12 and the mixing bag 11, plus a sodium chloride B bag 15. However, in this particular embodiment of the bag system, freezing bag 12 has only a single freezing chamber 10. Freezing chamber 10 has a removal adapter 13, which permits the sterile removal of the transported or stored liquid contents of the chamber.

Figure 8:
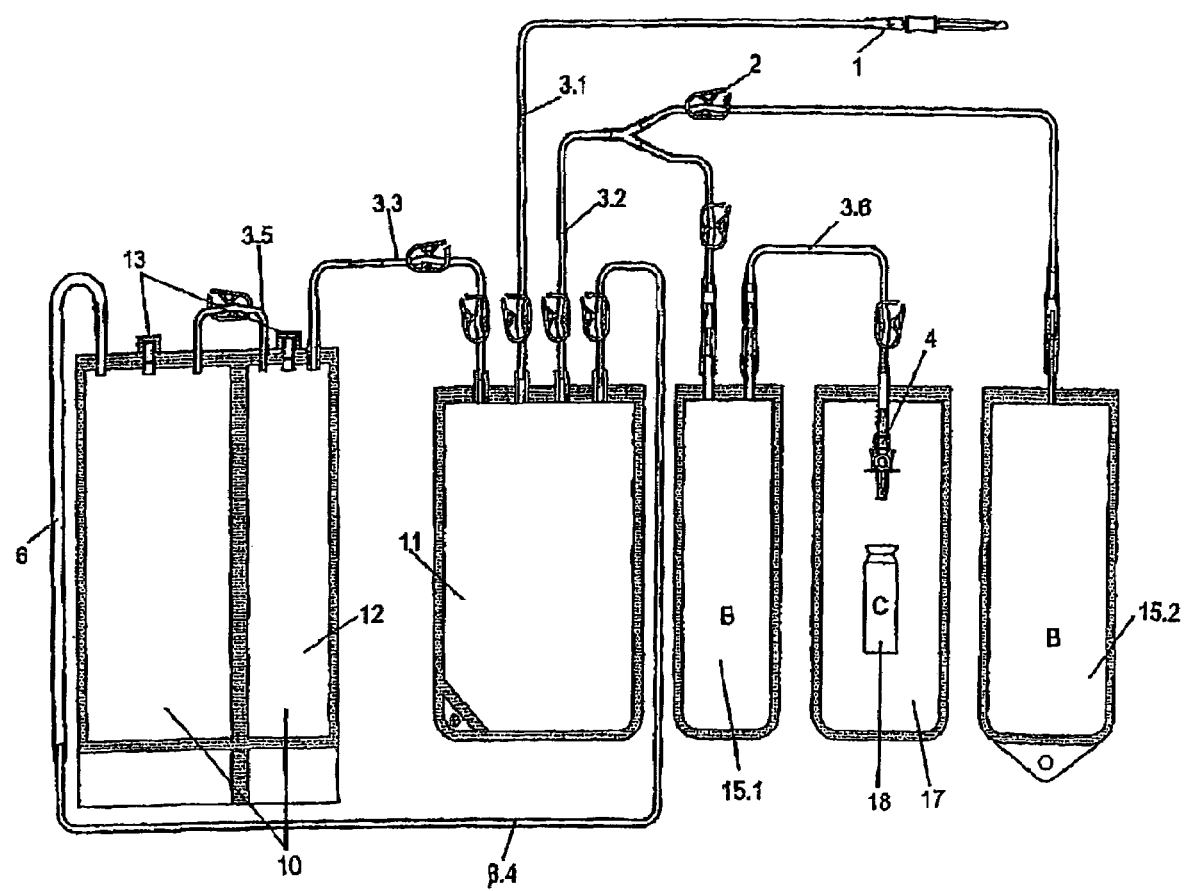
FIG. 8 shows an embodiment of the bag system, having a mixing bag 11 and freezing bag 12, wherein there are two chambers, and two connecting lines 3.3 and 3.4 between the freezing bag 12 and the mixing bag 11, plus two sodium chloride B bags 15.1 and 15.2, and also having a protective bag 17, within which there is a glass ampoule 18.

The embodiment represented in FIG. 8 is a bag system, having a mixing bag 11, which is connected in a communicating manner by four connecting lines 3.1, 3.2, 3.3 and 3.4 to a collection device 1 for the direct collection of umbilical cord blood, a freezing bag 12 and two bags 15.1 and 15.2, respectively. Each freezing chamber 10 has a removal adapter 13, which permits the sterile removal of the transported or stored liquid contents of the chamber. The communication, i.e., in particular the liquid transport and the air exchange, between the aforementioned components of the bag system is realized by opening or closing multiple shut-off elements 2, which permit a sealable interruption of flow in each line. In accordance with the methods provided herein, the liquid media, possibly with air inclusions, are transported within the bag system by gravity and by exertion of manual pressure on the flexible walls of the bags.

Inlet element 4, which in the configuration shown in FIG. 7 is a tapping pin for a pierceable stopper of glass ampoule 18, serves for the sterile introduction of a liquid cryoprotectant C, for example, in an exemplary method 10 ml of DMSO. Glass ampoule 18 is contained within hermetically sealed protective bag 17, which bag is connected to the bag 15.1 via connecting line 3.5. In an exemplary practice, bag 15.1, having a capacity in an exemplary method of about 20 ml, contains an amount of about 10 ml of a sodium chloride solution. With respect to the connecting lines 3.2 and 3.6, bag 15.1 is in each case sealable from the remainder of the system by an interruption valve 2. In an exemplary method, bag 15.2, which is connected by connecting line 3.2 to bag 15.1 and mixing bag 11, may be sealed from the remainder of the system by an interruption valve 2. In an exemplary method using this particular embodiment, bag 15.2 contains 100 ml of a sodium chloride solution. After the introduction of the umbilical cord blood and/or liquids which permit and/or assist cryopreservation, connecting lines 3.1 and 3.2 can be hermetically sealed and/or separated by welding, as above.

Like connecting lines 3, flexible mixing bag 11 (in this and in other embodiments) substantially consists of a plasticized PVC plastics material or other equivalent material known in the art for this purpose, which can be sterilized in a way known, such as by autoclaving, gamma radiation or the like. Transparent mixing bag 11 is designed in this particular exemplary embodiment to hold a maximum volume of 180 ml. Freezing bag 12 substantially consists of an EVA plastics material (as are all freezing bags 12 in the figures presented herein), and has two freezing chambers 10. Each freezing chamber 10 has a removal adapter 13, which permits the sterile removal of the stored liquid mixture. Connecting lines 3.3 and 3.4 connect mixing bag 11 and chambers 10 of freezing bag 12 to each other. One of the thin-walled, flexible and transparent connecting lines 3.3 or 3.4 may also be a region for storing the mixture of liquids and body fluid in small segments 6, as described in the embodiment shown in FIG. 5. These segments 6, for example in an exemplary method there are five of them, with a capacity in each case of about 1 ml. The segments 6 are hermetically sealable and separable from one another and the remainder of the system (not shown in FIG. 8), can be produced by welding from part of the connecting line 3.3 or 3.4.

The two freezing chambers 10 are connected to each other in a communicating manner by connecting line 3.5. After the hermetic sealing and separating connecting lines 3.3, 3.4 and 3.5 from mixing bag 11 and freezing bag 12, the two freezing chambers 10 are separable from each other.

Figure 9:
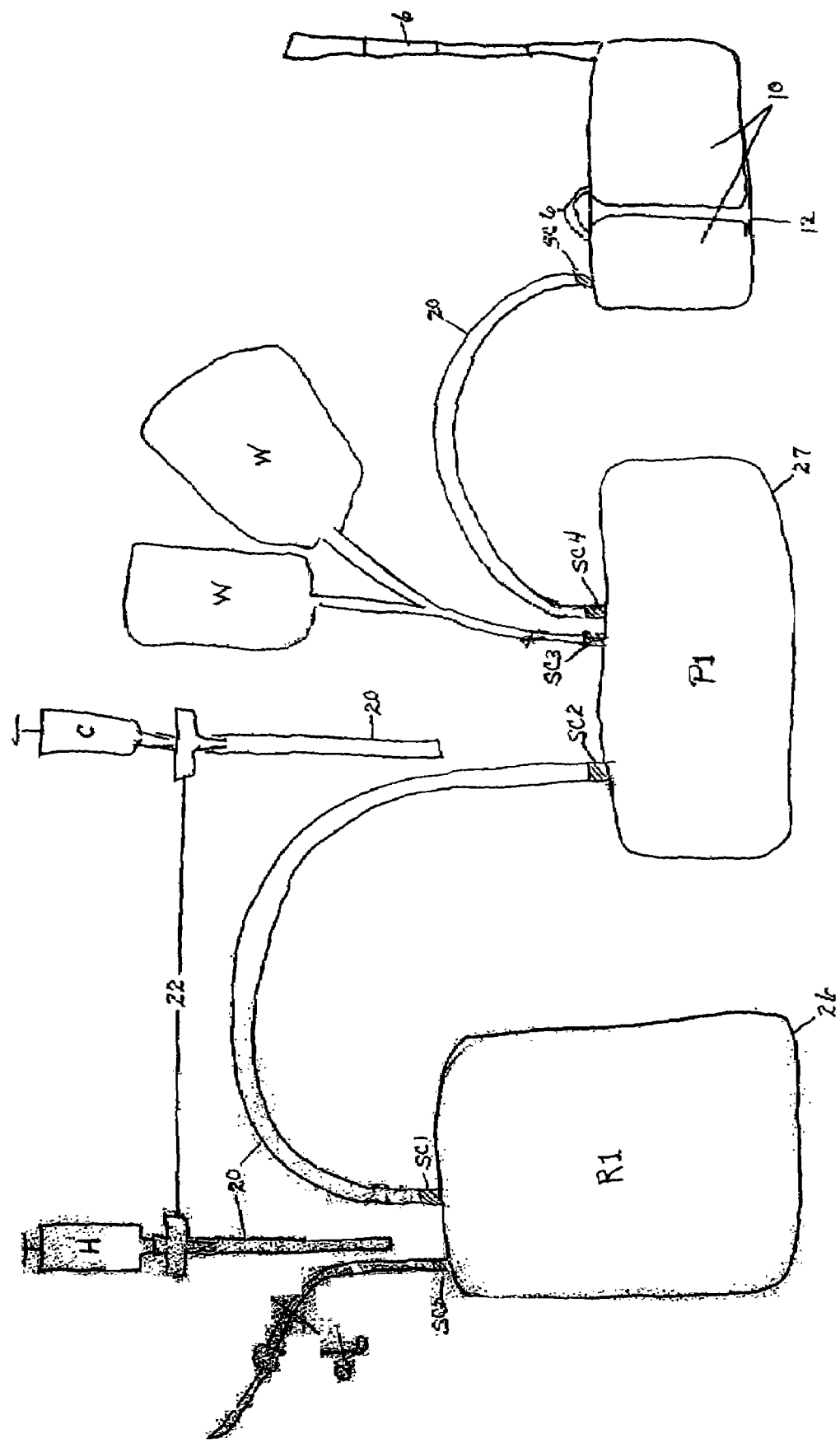
FIG. 9 show a bag system and sterile connections of a preferred embodiment of the present invention that can be added to the bag systems of any of the embodiments described herein or shown in the foregoing figures, to permit additional fluids to be added or removed, while at all times maintaining the sterility of the system.

In another preferred embodiment, a method is provided to introduce one or more fluids into the closed, sterile transporting and/or storing system, such as the bag system of the present invention. FIG. 9 shows an embodiment of the bag system, having additional sterile connections SC1, SC2, SC3, and SC4 (additional sterile connectors could be used in other embodiments depending upon the number of bag components used) to permit expansion of the system. Prior to storage, fluids are collected into the system via one or more inlet elements 4 integral to the particular bag system used. The inlet elements are then separated from and/or removed from the bag system.

In an exemplary method of using the embodied system shown in FIG. 9, biological fluids are introduced into the bag system via inlet element 1. After the introduction of the biological fluids through inlet element 1, the connecting line forming a part of inlet element 1 and connecting it to mixing bag 11 is hermetically sealed or separated, e.g., by welding, as above. Likewise, after the introduction of a fluid or liquid through the one or more inlet elements 4 that are integral to the bag system, the corresponding connecting lines 3 to the one or more mixing or freezing bags are hermetically sealed. Inlet element 4 may then be removed from the bag assembly to minimize the components and space needed for storage of the bag system.

This exemplified method thus provides a means for introducing one or more fluids into the bag system, without using those inlets 4 that are initially integral to the bag system, while at the same time, maintaining the closed, sterile system. As shown in the embodiment provided in FIG. 9, one or more fluids are introduced into the bag system via one or more connection assemblies 20. Connection assembly 20 comprises sterile filter 22 and connection tube 23. The components of connection assembly 20 are commercially available parts suitable for the specific application of the bag system and fluid being introduced. For example, in a preferred embodiment, filter 22 is a DMSO filter 25 mm FLL Nylon 0.2 ml filter (e.g., DMSO-Safe Acrodisc® Sterile Syringe Filter (PALL Medical, Phoenix, Ariz.), made from polypropylene housing with a PA nylon filter mesh), and connection tube 23 is 3.1×4.0×100 mm PVC tube. All materials are tested for biocompatibility and meet the specifications of USP Class VI as well as hemolysis test. One skilled in the art would know of alternate components that may be used for filter 22 and connection tube 23.

DMSO filter is attached to the PVC tubing using adhesive, for example, Loctite 3301 (isobornyl-acrylate adhesive) (Loctite, Henkel, Germany), which is also used for attaching other components together, wherein such connections will over time be exposed to DMSO or other solvents. This particular adhesive is a one component UV curing material. The material complies with biocompatibility tests according to ISO 10993, such as cytotoxicity test, acute systemic toxicity test, intracutaneous toxicity test and implantation test.

As shown in FIG. 9, each fluid connection assembly 20 is attached to a connecting line 3 of the bag assembly by sterile connections SC1 and SC3. Sterile connections SC1 and SC3 are formed by joining together tube 23 of fluid connection assembly 20 and a connecting line 3 of the bag system by a sterile joining technique authorized for human medicine as known in the art (e.g., Model 3900 Sterile Tubing Connector, SEBRA). For example, the tubes may also be connected by welding or joining by using a transportable film-welding appliance, as above.

Fluid is introduced to the bag system through connection assembly 20 by a syringe, of a type that is commercially available for such purposes, and of a size and material suitable for the particular application, and designed to transport sterile fluids. In particular embodiments, the syringe is also sized to mate with filter 22. For example, in a preferred embodiment where DMSO is the cryopreservative fluid being introduced, an Omniflex-Syringe 20 ml/50 ml (B. Braun, Melsungeer, Germany) may be used.

Alternatively, as shown in the embodiment of FIG. 9, the same sterile connection technique using connectors SC1 and SC4, as above, is used to join a connecting lines 3 of the bag system with another tube, such as, an inlet tube for collection into the system or an exit tube for waste removal. By using sterile connection SC4, the bag system can be modified to introduce additional sterile fluids, to remove additional fluids from the bag system, and to move fluids into separate regions of the bag system while always maintaining a closed, sterile system. Indicators 7 may be used to show fill lines or other information on the bag system components as described above, but not shown. Thus, this preferred embodiment advantageously permits the addition of additional systems to the existing closed sterile bag system after it has been prepared as set forth in the embodiments describe above. Yet at all times, the sterility of the expanded system is maintained without the need of operating in an ultra-clean room. Likewise expansion of the system, in accordance with the preferred embodiments, will permit removal of parts of the expanded system (e.g., to remove waste and bulk) once the purpose of the removed component has been served—but at no time is the sterility of the closed bag system breached.

Accordingly, as shown in the embodiment provided in FIG. 9, sterile connection SC1 joins the inlet tube from inlet element 1 to a sterile tube of a first connection assembly 20. A first fluid can then be introduced through a first syringe through connection assembly 20 into the bag system. Sterile connection SC2 provides a connection between a collection bag 26 (containing e.g., region R1) and a processing or separation bag 27 (containing e.g., region P1). Sterile connection SC3 provides a sterile connection to introduce a second fluid or mixture into processing or separation bag 27.

In practice of an exemplary method of using the preferred embodiment shown in FIG. 9, a body fluid, such as blood, is collected from the body and introduced into the bag system through inlet 1 to region R1. A first fluid H, e.g., 50 ml HESpan (B. Braun), or dextran (amount depends on the volume of blood or biological fluid that has been collected), is introduced from input bag 14 containing H, through a first connection assembly 20 via sterile connection SC1 to region R1. The mixture of HES (hydroxyethylene starch) and the biological fluid in region R1 is then moved to processing and separation bag P1 via sterile connection SC2. A second fluid (e.g., 5 ml DMSO) is introduced into P1 of to the bag system through a second connection assembly 20 via sterile connection SC3. The mixture in processing and separation bag P1 is then processed and separated into layers, such as, but without limitation, a layer of excess HES, a layer of excess serum and a layer of enriched white blood cells. Using another connection assembly 20 and sterile connection SC4, the fluids or mixture in processing and separating bag P1 can be separately moved to one or more waste collecting bags W to remove the excess HES and excess serum, or the biologically valuable fluid is moved through another connection assembly 20 via sterile connection SC6 to a freezing bag 12, having one or more chambers 10, for cryopreservation and storage.

A line used as a connection assembly 20 line, may be added as shown in FIG. 9 and used as described in FIG. 8, i.e., to divide into segments 6, (4 such segments are shown, but only by example). Each segment may have a defined capacity of e.g., 1 ml, and each is hermetically sealable and separable from one another and from the remainder of the system. Segments 6 can be produced as described above, and cryopreserved without removal for future use in testing aliquots without breaching the sterility of the expanded closed sterile system.

In an alternative method of using the embodiment of FIG. 9, rather than collecting biological fluid through 1, the bag system is connected by sterile technique to a preformed sterile system by another connection assembly 20 and sterile connector SC5. This permits movement of fluids and mixtures of cells and fluids in the preformed system to be moved into or from the expanding bag portion (FIG. 9) from the preformed part of the now expanded system, without a need for clean room conditions and without a breach in sterility of the now expanded system. In one embodiment, non-viscous fluids, such as DMSO (e.g., 60% in NaCl), are transported from input container 14, through a connection filtration assembly 22 (as shown in the delivery of fluid C). Thus, the fluid entering the closed system is sterile before introduction directly into the bag system, and allows movement of the sterile fluid between elements of the bag system.

In an alternative embodiment, the fluid may already be sterile. Once the sterile connection SC is made, fluid is introduced into the bag system while maintaining a closed, sterile system. Such introduction methods are necessary for viscous fluids, such as HES, as shown as H in input container 14. Accordingly, a method is provided to introduce one or more fluids to the bag system via a sterile connection without a pre-existing port.

In yet another embodiment, parts of the expanding, sterile bag system may not be used in the expanded sterile system and may be sealed or clamped off from the remainder of the system, such as by shut-off elements 2 (not shown), used as described in the foregoing embodiments shown in other figures. In other words, the system may be used, for example, without limitation, to introduce HES, or not; or to introduce additional DMSO, or not; or to introduce only one fluid and also to remove one waste product. The sterile filters 22 may be in yet another alternative embodiment be used to vent air from the system, as opposed to introducing fluids. In such an embodiment, input bag 14 may be removed to permit the vented air to escape (not shown).

Accordingly, many variations are possible and the purpose of the expanding bag system is to permit variable additions to the expanded system and use those components that are necessary without the need for ultra-clean room conditions, without breaching sterility of the system, and without the use of pre-existing ports on the preformed system. The materials used are selected as above, for example the material of the freezing bag is the same as previously described for 12, filters 22 are as described for sterile filtration, and the like. A protective enclosure 8 may be added around the entire expanded system or simply around any part thereof, such as only those sections that will actually be subject to cryopreservation (not shown).

Figure 10:
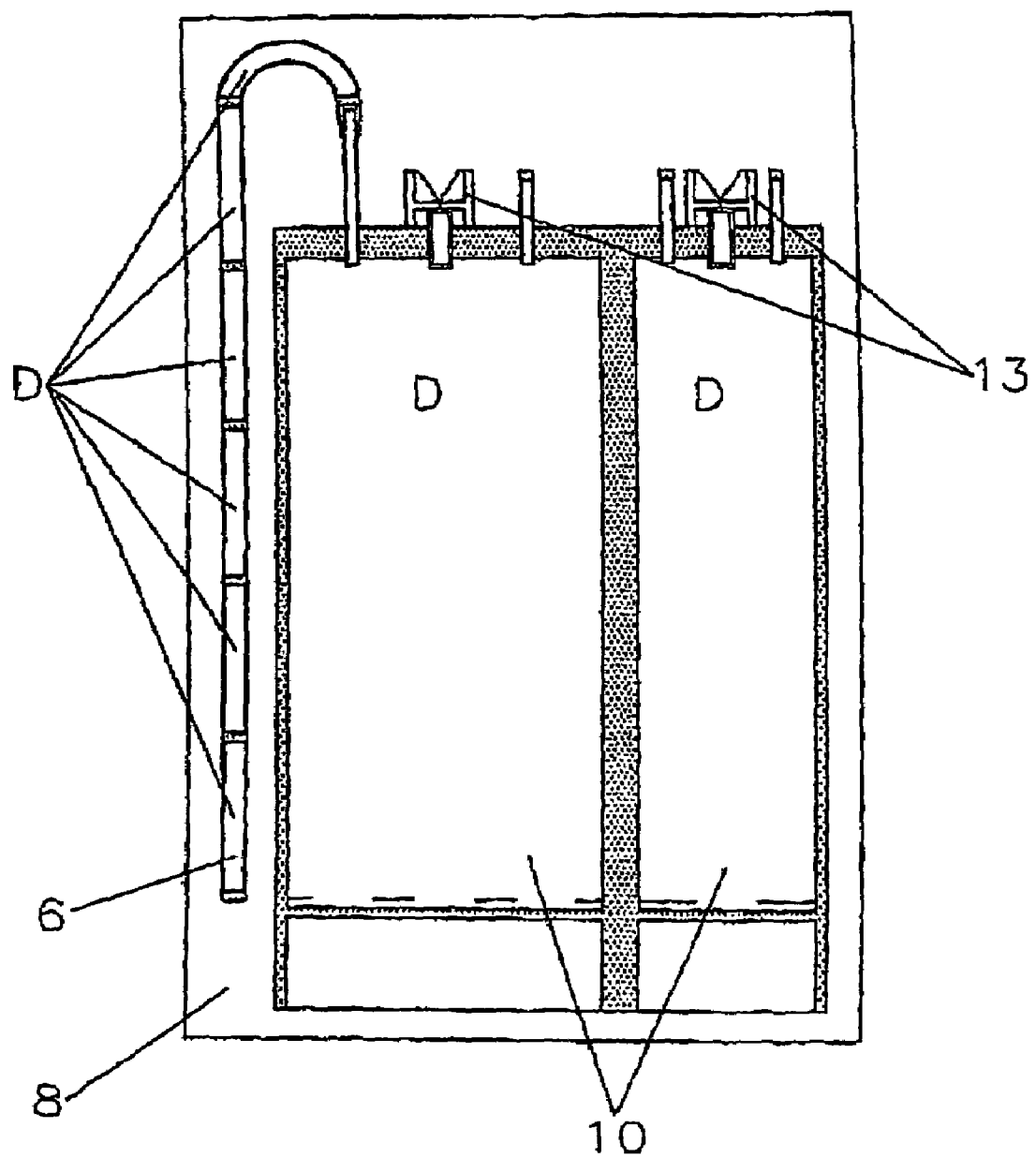
FIG. 10 shows the parts of an embodiment of the bag system that are used for cryopreservation of liquids and fluids contained therein, while still maintaining the sterility of the system.

FIG. 10 shows parts of a bag system before freezing. It can represent the freezing bag in any embodiment or in the exemplary embodiments described in the figures set forth herein. After the separation of those hermetically sealed parts of a bag system that are to be passed on for cryopreservation (i.e., one or two chambers of freezing bag 12 or of mixing and freezing bag 16 and/or one or more segments 6 of a connecting line 3, which contain a liquid mixture D comprising umbilical cord blood and liquids which permit and/or assist cryopreservation) the aforementioned parts of the bag system are introduced into an enclosure 8. Enclosure 8, which serves in particular for protection from mechanical damage, comprises a very cold temperature-resistant plastic film, which is sealed in a gas-tight manner by welding.

The present invention is further described in the following examples in which experiments were conducted to validate the methods of introducing one or more liquids into the bag system through a sterile connection. These examples are provided for purposes of illustration to those skilled in the art, and are not intended to be limiting unless otherwise specified. Moreover, these examples are not to be construed as limiting the scope of the appended claims. Thus, the invention should in no way be construed as being limited to the following examples, but rather, should be construed to encompass any and all variations which become evident as a result of the teaching provided herein.

EXAMPLES

Example 1

Method Introducing Sterile Fluid and Maintaining Sterility of the System

To confirm the methods for introducing one or more fluids into the previously assembled bag system of the present invention, studies were conducted introducing various fluids into the bag system using the fluid connection assembly and a sterile connection technique. The intent of the filter of the fluid connection assembly is to ensure that the fluid introduced into the bag system is sterile. In a first study, the passage of hydroxyethylstarch (HES) through the filter of the fluid connection assembly was tested. The filter used was a DMSO-Safe Acrodisc® Sterile Syringe Filter, although suitable filters may also be produced by other manufacturers.

An initial study found that after the passage of approximately 2.0 ml, the HES clotted and additional fluid could not pass through the filter. In certain cryopreservation applications, a larger quantity of HES is required for the preparation of the body fluids for storage. For example, in the cryopreservation and storage of a sample of umbilical cord blood (30-200 ml), a standard of approximately 50 ml of HES is required.

Consequently, the sterile HES (or other viscous fluid) was provided in a separate sterile bag. A sterile amount of HES was, therefore, added to the bag system directly through a sterile connection, without filter. For example, a 50 ml bag of sterile HES was provided with a tube attached to the bag. The tube of the HES bag was connected to a connecting line of the bag system by a sterile connection technique as know in the art. The sterile HES is then directly introduced into the bag system.

In another study, the passage of serum was tested. Like the HES, the serum is viscous and clotted when passed through the filter. Thus, for these and other similar fluids, the fluid must be provided in sterile form, and introduced directly into the bag system via a sterile connection technique.

Example 2

Method of Sterilizing at Introduction

In other studies, the connection assembly with a filter was tested for the passage of dimethyl sulfoxide (DMSO), alone and in combination with other fluids. In one test, 5 ml of DMSO passed through the filter of the connection assembly without clotting. The filter used was as above.

In another test, a mixture of DMSO and plasma immediately clotted the filter. Thus, volume adjustments with plasma are made by sterile connecting a sterile syringe (20 ml) with the plasma bag. The required amount of plasma is aspirated, and then sealed off. A connection is made with the storage bag, injected and then a defined amount (5 ml) 50% DMSO/saline is added through the sterile connected DMSO filter.

In a third test, DMSO was mixed with serum. In this test, sixty percent (60%) of the mixture passed through the filter assembly of the type described above. These studies demonstrated that 60% of a DMSO mixed with serum or other isotonic fluid, passed through the filter without clotting.

For these fluids, or mixtures of fluids, a connection assembly is used to introduce the fluid, or mixture, into the bag system. The connection assembly was attached to the bag system by sterile connection techniques as known in the art. By passing the fluid through the filter of the connection assembly, the fluid was sterilized prior to entering or mixing with fluid in the bag system. As a result, preferred embodiments of the present invention provide systems that permit the addition of additional systems to the existing sterile bag system set forth in the embodiments describe above, while at all times maintaining sterility without the need of doing so in an ultra-clean room, and likewise will permit removal of the additional system once its purpose has been served without breaking the sterility of the closed bag system. Methods for the use of the preferred embodiments permit additional sterile liquids to be added or waste products removed from the bag system after its initial assembly, without the need for ultra-clean facilities.

The disclosures of each patent, patent application and publication cited or described in this document are hereby incorporated herein by reference, in their entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

I claim:

1. A method for forming an expandable closed, sterile bag system to be used for collecting, transporting and storing a biological fluid and the cells contained therein, the method comprising:

providing a sterile, closed bag system, constructed for long-term exposure to biological fluid, the system having at least one inlet element and at least one outlet element; a plurality of sterile communicable components or compartments, separably connected to one another for holding, receiving, mixing, transporting, cryopreserving or storing biological fluid/cells in sterile form; one or more regions for containing or mixing liquid(s) and biological fluid(s) and for storing same; at least one closable air vent for removing air from one compartment to another within the system without opening the closed system; and shut-off elements and connecting lines communicably connecting parts of the bag system to maintain a closed, sterile system, and wherein the regions for storing contents of the bag system are hermetically sealable and separable from one another;

providing at least one sterile fluid expansion connection assembly, comprising a sterile filter for sterile filtration of fluids added to the system, and sterile tube in sterile combination; and operably, connectably and sterilely attaching the tube end of the at least one expansion connection assembly to the bag system to provide at least one sterile expansion connecting assembly extending from the sterile, closed bag system.

2. The method of claim 1, wherein the filter comprises a microporous, sterile filter.

3. The method of claim 1, wherein the tube comprises poly(-vinyl) chloride.

4. The method of claim 1, wherein the sterile components and compartments, and each connection assembly and part of the bag system of the expandable system are designed to withstand extended exposure to one or more cryopreservatives.

5. The method of claim 4, wherein the cryopreservative is DMSO.

6. The method of claim 1, wherein the sterile components and compartments, and each connection assembly and part of the bag system of the expandable system for use in cryopreserving biological fluid and the cells contained therein, are designed to withstand extended periods of time at cryopreservation temperatures.

7. The method of claim 1, further comprising sterilizing additional fluids to be added to biological fluids/cells in the bag system before sterilely adding the additional fluids to the closed, preformed, sterile system, while maintaining sterility of the system.

8. A method for forming an expandable closed, sterile bag system to be used for collecting, transporting and storing a biological fluid and the cells contained therein, the method comprising:

providing a sterile, closed bag system, constructed for long-term exposure to biological fluid, the system having at least one inlet element and at least one outlet element; a plurality of sterile communicable components or compartments, separably connected to one another for holding, receiving, mixing, transporting, cryopreserving or storing biological fluid/cells in sterile form; one or more regions for containing or mixing liquid(s) and biological fluid(s) and for storing same; at least one closable air vent for removing air from one compartment to another within the system without opening the closed system; and shut-off elements and connecting lines communicably connecting parts of the bag system to maintain a closed, sterile system, and wherein the regions for storing contents of the bag system are hermetically sealable and separable from one another;

providing at least one sterile expansion connection assembly for fluids, the assembly comprising a sterile filter for sterile filtration of fluids added to the system, and blind-sealed, sterile tube extending therefrom; and operably and connectably attaching the tube of the at least one expansion connection assembly to the closed, sterile bag system by sterile connection without opening the closed bag system, thereby sealing the at least one expansion connecting assembly to and extending from the closed, sterile bag system.

9. The method of claim 8, wherein the filter comprises a microporous, sterile filter.

10. The method of claim 8, wherein the tube comprises poly(-vinyl) chloride.

11. The method of claim 8, wherein the sterile components and compartments, and each connection assembly and part of the bag system of the expandable system are designed to withstand extended exposure to one or more cryopreservatives.

12. The method of claim 11, wherein the cryopreservative is DMSO.

13. The method of claim 8, wherein the sterile components and compartments, and each connection assembly and part of the bag system of the expandable system for use in cryopreserving biological fluid and the cells contained therein, are designed to withstand extended periods of time at cryopreservation temperatures.

14. The method of claim 8, further comprising sterilizing additional fluids to be added to biological fluids/cells in the bag system before sterilely adding the additional fluids to the closed, preformed, sterile system, while maintaining sterility of the system.

* * * * *